(12) United States Patent
Saksena et al.

(10) Patent No.: US 8,377,891 B2
(45) Date of Patent: Feb. 19, 2013

(54) PROCESS FOR SYNTHESIS OF CYCLIC OCTAPEPTIDE

(75) Inventors: Divya Lal Saksena, Mumbai (IN); Digamber Shripati Pawar, Mumbai (IN); Nikhil Umesh Mohe, Mumbai (IN); Nilesh Dagdu Patil, Mumbai (IN); Chandrakesan Muralidharan, Mumbai (IN); Lester Lobo, Mumbai (IN); Radhakrishnan Venkatasubramanian Tarur, Mumbai (IN)

(73) Assignee: USV, Ltd., Mumbai (IN)

( * ) Notice: Subject to any disclaimer, the term of this patent is extended or adjusted under 35 U.S.C. 154(b) by 0 days.

(21) Appl. No.: 13/123,623

(22) PCT Filed: May 4, 2009

(86) PCT No.: PCT/IN2009/000263
§ 371 (c)(1),
(2), (4) Date: Apr. 11, 2011

(87) PCT Pub. No.: WO2010/089757
PCT Pub. Date: Aug. 12, 2010

(65) Prior Publication Data
US 2012/0035117 A1    Feb. 9, 2012

(30) Foreign Application Priority Data
Nov. 7, 2008 (ID) .......................... 2366/MUM/2208

(51) Int. Cl.
*A61K 38/08*    (2006.01)
(52) U.S. Cl. ..................................... 514/21.7
(58) Field of Classification Search .................... None
See application file for complete search history.

(56) References Cited

U.S. PATENT DOCUMENTS

| | | | |
|---|---|---|---|
| 4,395,403 A | 7/1983 | Bauer et al. | |
| 5,102,985 A | 4/1992 | Niwa et al. | |
| 5,656,721 A | 8/1997 | Mergler et al. | |
| 5,889,146 A | 3/1999 | Lee et al. | |
| 6,316,414 B1 * | 11/2001 | Burman et al. | 514/19.3 |
| 6,346,601 B1 | 2/2002 | Obiols et al. | |
| 6,476,186 B1 | 11/2002 | Hsieh et al. | |
| 6,987,167 B2 | 1/2006 | Chaturvedi et al. | |
| 2004/0249121 A1 | 12/2004 | Tovi et al. | |
| 2007/0297979 A1 * | 12/2007 | Lovhaug | 424/1.69 |
| 2008/0097079 A1 | 4/2008 | Quattrini et al. | |
| 2010/0021487 A1 | 1/2010 | Zorilla et al. | |

FOREIGN PATENT DOCUMENTS

| | | |
|---|---|---|
| EP | 0953577 * | 11/1999 |
| WO | WO2005/087794 A1 | 9/2005 |

OTHER PUBLICATIONS

Sidorova et al., Russian J. Of Bioorg. Chem. vol. 2004.*
Goumass et al., The Oncologist 1998, p. 50.*
Storch et al., The Journal of Nuclear Medicine vol. 46 No. 9, Sep. 2005.*
Sidorova, et al., "The Use of Hydrogen Peroxide for Closing Disulfide Bridges in Peptides," Russian Journal of Bioorganic Chemistry, (2004) vol. 30, No. 2., p. 101-110. (Abstract Only).
Wang, W., et al., "Large SCale Synthesis of Octreotide," Fine Chemicals (2007), vol. 24, No. 10, p. 1033-1036. (Abstract Only).
Alsina, J., et al., "Active Carbonate Resins for Solid-Phase Synthesis Through the Anchoring of a Hydroxyl Function. Synthesis of Cyclic and Alcohol Peptides," Tetrahedron Letters, (1997) 38(5) p. 883-886.
Edwards, B.W., et al., "Generally Applicable, Convenient Solid-Phase Synthesis and Receptor Affinities of Octreotide Analogs," J. Med. Chem. (1994) 37, p. 3749-3757.

* cited by examiner

*Primary Examiner* — Cecilia J Tsang
*Assistant Examiner* — Kaipeen Yang
(74) *Attorney, Agent, or Firm* — Pharmaceutical Patent Attorneys, LLC

(57) ABSTRACT

This invention relates a process for preparing octreotide and derivatives thereof. The starting material, Cys(Trt)-2-Chlorotrityl resin is coupled with various amino acids to obtain a protected heptapeptide of formula (2): Boc-D-Phe-Cys(Trt)-Phe-D-Trp-Lys(Boc)-Thr(OBut)-Cys(Trt)-2-Chlorotrityl resin. The linear protected peptide of formula (2) is cleaved from the support using TFA5TIS and water to yield linear protected peptide of formula (3) Boc-D-Phe-Cys(Trt)-Phe-D-Trp-Lys(Boc)-Thr(OBut)-Cys(Trt)-OH Linear protected heptapeptide of formula (3) is deprotected to yield heptapeptide of formula (6): D-Phe-Cys-Phe-D-Tip-Lys-Thr-Cys-OH; which is cyclized using hydrogen peroxide and to the cyclic peptide of formula (7) D-Phe-Cys-Phe-D-Trp-Lys-Thr-Cys-OH; threoninol is coupled at C terminal to yield octreotide. Alternatively threoninol is coupled to the heptapeptide of formula (3) to yield protected octapeptide of formula (4) Boc-D-Phe-Cys(Trt)-Phe-D-Trp-Lys(Boc)-Thr(OBut)-Cys(Trt)-Thr-OL which is subsequently deprotected to yield linear octapeptide of formula (5) D-Phe-Cys-Phe-D-Trp-Lys-Thr-Cys-Thr-OL and cyclized with hydrogen peroxide to yield cyclic octreotide with a yield of >95%.

Figure 1:
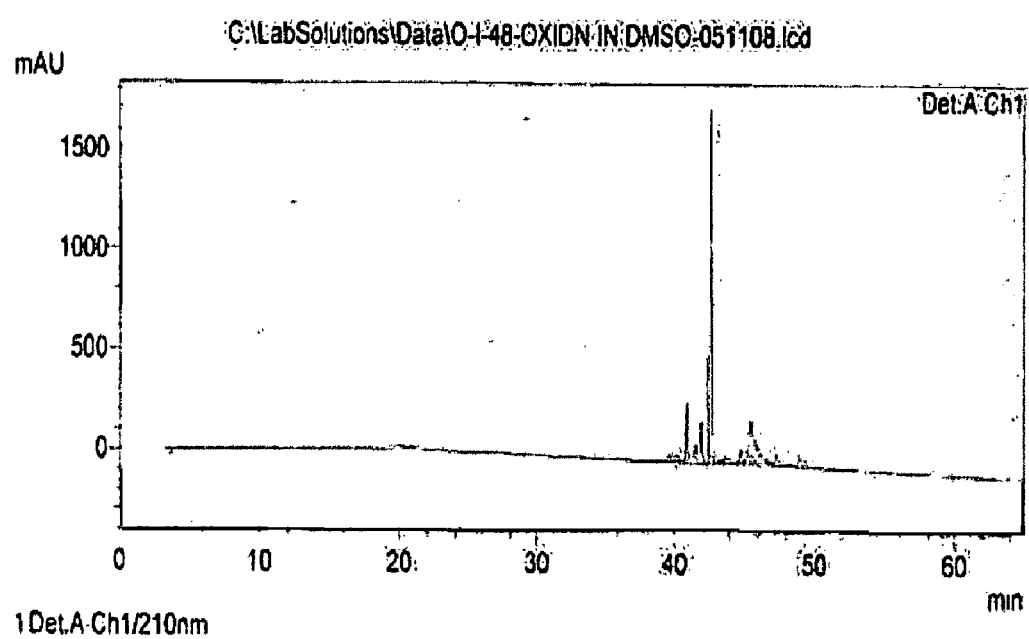

(2)
Boc-D-Phe-Cys(Trt)-Phe-D-Trp-Lys(Boc)-Thr-(OBut)-Cys(Trt)-2-Chlorotrityl resin.

(3)
Boc-D-Phe-Cys(Trt)-Phe-D-Trp-Lys(Boc)-Thr-(OBut)-Cys(Trt)-OH (6)
D-Phe-Cys-Phe-D-Trp-Lys-Thr-Cys-OH;
            |                    |
            SH                   SH (7)
D-Phe-Cys-Phe-D-Trp-Lys-Thr-Cys-OH;
            |                    |
            S————————————————————S (4)
Boc-D-Phe-Cys(Trt)-Phe-D-Trp-Lys(Boc)-Thr-(OBut)-Cys(Trt)-Thr-OL, (5)
D-Phe-Cys-Phe-D-Trp-Lys-Thr-Cys-OL
            |                    |
            SH                   SH

13 Claims, 6 Drawing Sheets

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial
<220> FEATURE:
<223> OTHER INFORMATION: completely synthesized
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: DISULFID
<222> LOCATION: (2)..(7)
<220> FEATURE:
<221> NAME/KEY: MISC_FEATURE
<222> LOCATION: (4)..(4)
<223> OTHER INFORMATION: D-Tryptophan
<220> FEATURE:
<221> NAME/KEY: MISC_FEATURE
<222> LOCATION: (8)..(8)
<223> OTHER INFORMATION: threoninol

<400> SEQUENCE: 1

Phe Cys Phe Trp Lys Thr Cys Thr
1               5

<210> SEQ ID NO 2
<211> LENGTH: 7
<212> TYPE: PRT
<213> ORGANISM: Artificial
<220> FEATURE:
<223> OTHER INFORMATION: completely synthesized
<220> FEATURE:
<221> NAME/KEY: MISC_FEATURE
<222> LOCATION: (1)..(1)
<223> OTHER INFORMATION: tert-butyloxycarbonyl
<220> FEATURE:
<221> NAME/KEY: MISC_FEATURE
<222> LOCATION: (1)..(1)
<223> OTHER INFORMATION: D-Phenylanine
<220> FEATURE:
<221> NAME/KEY: MISC_FEATURE
<222> LOCATION: (2)..(2)
```

```
<223> OTHER INFORMATION: Trityl
<220> FEATURE:
<221> NAME/KEY: MISC_FEATURE
<222> LOCATION: (4)..(4)
<223> OTHER INFORMATION: D-Tryptophan
<220> FEATURE:
<221> NAME/KEY: MISC_FEATURE
<222> LOCATION: (5)..(5)
<223> OTHER INFORMATION: tert-butyloxycarbonyl
<220> FEATURE:
<221> NAME/KEY: MISC_FEATURE
<222> LOCATION: (6)..(6)
<223> OTHER INFORMATION: O-t-butyl
<220> FEATURE:
<221> NAME/KEY: MISC_FEATURE
<222> LOCATION: (7)..(7)
<223> OTHER INFORMATION: trityl-2-Chlorotrityl

<400> SEQUENCE: 2

Phe Cys Phe Trp Lys Thr Cys
1               5

<210> SEQ ID NO 3
<211> LENGTH: 7
<212> TYPE: PRT
<213> ORGANISM: Artificial
<220> FEATURE:
<223> OTHER INFORMATION: completely synthesized
<220> FEATURE:
<221> NAME/KEY: MISC_FEATURE
<222> LOCATION: (1)..(1)
<223> OTHER INFORMATION: tert-butyloxycarbonyl
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MISC_FEATURE
<222> LOCATION: (2)..(2)
<223> OTHER INFORMATION: Trityl
<220> FEATURE:
<221> NAME/KEY: MISC_FEATURE
<222> LOCATION: (4)..(4)
<223> OTHER INFORMATION: D-Trypotphan
<220> FEATURE:
<221> NAME/KEY: MISC_FEATURE
<222> LOCATION: (5)..(5)
<223> OTHER INFORMATION: tert-butyloxycarbonyl
<220> FEATURE:
<221> NAME/KEY: MISC_FEATURE
<222> LOCATION: (6)..(6)
<223> OTHER INFORMATION: O-t-butyl
<220> FEATURE:
<221> NAME/KEY: MISC_FEATURE
<222> LOCATION: (7)..(7)
<223> OTHER INFORMATION: trityl hydroxy

<400> SEQUENCE: 3

Phe Cys Phe Trp Lys Thr Cys
1               5

<210> SEQ ID NO 4
<211> LENGTH: 8
<212> TYPE: PRT
<213> ORGANISM: Artificial
<220> FEATURE:
<223> OTHER INFORMATION: completely synthesized
<220> FEATURE:
<221> NAME/KEY: MISC_FEATURE
<222> LOCATION: (1)..(1)
<223> OTHER INFORMATION: tert-butyloxycarbonyl
<220> FEATURE:
<221> NAME/KEY: MISC_FEATURE
<222> LOCATION: (1)..(1)
<223> OTHER INFORMATION: D-Phenylalanine
<220> FEATURE:
```

```
<221> NAME/KEY: MISC_FEATURE
<222> LOCATION: (2)..(2)
<223> OTHER INFORMATION: Trityl
<220> FEATURE:
<221> NAME/KEY: MISC_FEATURE
<222> LOCATION: (4)..(4)
<223> OTHER INFORMATION: D-Tryptophan
<220> FEATURE:
<221> NAME/KEY: MISC_FEATURE
<222> LOCATION: (5)..(5)
<223> OTHER INFORMATION: tert-butyloxycarbonyl
<220> FEATURE:
<221> NAME/KEY: MISC_FEATURE
<222> LOCATION: (6)..(6)
<223> OTHER INFORMATION: O-t-butyl
<220> FEATURE:
<221> NAME/KEY: MISC_FEATURE
<222> LOCATION: (7)..(7)
<223> OTHER INFORMATION: trityl
<220> FEATURE:
<221> NAME/KEY: MISC_FEATURE
<222> LOCATION: (8)..(8)
<223> OTHER INFORMATION: Threoninol

<400> SEQUENCE: 4

Phe Cys Phe Trp Lys Thr Cys Thr
1               5

<210> SEQ ID NO 5
<211> LENGTH: 8
<212> TYPE: PRT
<213> ORGANISM: Artificial
<220> FEATURE:
<223> OTHER INFORMATION: completely synthesized
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MOD_RES
<222> LOCATION: (2)..(2)
<223> OTHER INFORMATION: Reduced Sulfer
<220> FEATURE:
<221> NAME/KEY: MISC_FEATURE
<222> LOCATION: (4)..(4)
<223> OTHER INFORMATION: D-Tryptophan
<220> FEATURE:
<221> NAME/KEY: MOD_RES
<222> LOCATION: (7)..(7)
<223> OTHER INFORMATION: Reduced Sulfer
<220> FEATURE:
<221> NAME/KEY: MISC_FEATURE
<222> LOCATION: (8)..(8)
<223> OTHER INFORMATION: Threoninol

<400> SEQUENCE: 5

Phe Cys Phe Trp Lys Thr Cys Thr
1               5

<210> SEQ ID NO 6
<211> LENGTH: 7
<212> TYPE: PRT
<213> ORGANISM: Artificial
<220> FEATURE:
<223> OTHER INFORMATION: completely synthesized
<220> FEATURE:
<221> NAME/KEY: MISC_FEATURE
<222> LOCATION: (1)..(1)
<223> OTHER INFORMATION: D-Phenylalanine
<220> FEATURE:
<221> NAME/KEY: MOD_RES
```

```
<222> LOCATION: (2)..(2)
<223> OTHER INFORMATION: Reduced Sulfer
<220> FEATURE:
<221> NAME/KEY: MISC_FEATURE
<222> LOCATION: (4)..(4)
<223> OTHER INFORMATION: D-Tryptophan
<220> FEATURE:
<221> NAME/KEY: MOD_RES
<222> LOCATION: (7)..(7)
<223> OTHER INFORMATION: Reduced Sulfer
<220> FEATURE:
<221> NAME/KEY: MOD_RES
<222> LOCATION: (7)..(7)
<223> OTHER INFORMATION: cysteine hydroxy
<220> FEATURE:
<221> NAME/KEY: MOD_RES
<222> LOCATION: (7)..(7)
<223> OTHER INFORMATION: cysteine

<400> SEQUENCE: 6

Phe Cys Phe Trp Lys Thr Cys
1               5

<210> SEQ ID NO 7
<211> LENGTH: 7
<212> TYPE: PRT
<213> ORGANISM: Artificial
<220> FEATURE:
<223> OTHER INFORMATION: completely synthesized
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: DISULFID
<222> LOCATION: (2)..(7)
<220> FEATURE:
<221> NAME/KEY: MISC_FEATURE
<222> LOCATION: (4)..(4)
<223> OTHER INFORMATION: D-Tryptophan
<220> FEATURE:
<221> NAME/KEY: MOD_RES
<222> LOCATION: (7)..(7)
<223> OTHER INFORMATION: cysteine hydroxy

<400> SEQUENCE: 7

Phe Cys Phe Trp Lys Thr Cys
1               5
```

PROCESS FOR SYNTHESIS OF CYCLIC OCTAPEPTIDE

RELATED APPLICATIONS:

This application claims priority from PCT Application No. PCT/IN2009/000263 filed on May 4, 2009, which in turn claims priority from Indian Provisional Application No. 2366/MUM/2008 filed on Nov. 7, 2008.

TECHNICAL FIELD

The present invention relates to the novel process for the synthesis of octreotide and derivatives thereof by solid phase peptide synthesis. In particular, the present invention relates to synthesis of protected linear peptides, cleavage from the resin, deprotection followed by cyclization process for the unprotected peptide wherein the preparation process is simple, easy, environment friendly, inexpensive with high yield and purity.

BACKGROUND OF INVENTION

Octreotide is a highly potent and pharmacologically selective analog of somatostatin. It inhibits growth hormone for long duration and is thereof indicated for acromegaly to control and reduce the plasma level of growth hormone. The presence of D-Phe at the N-terminal and an amino alcohol at the C-terminal, along with D-Tryptophan and a cyclic structure makes it very resistant to metabolic degradation.

Octreotide comprises 8 amino acids which has the following structural formula:

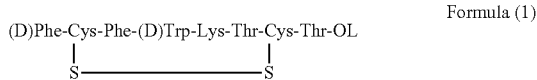

Formula (1)

wherein sulphur atoms of the Cys at the position 2 and of the Cys at the position 7 are mono-cyclic to form an —S—S— bridge.

A considerable number of known, naturally occurring small and medium-sized cyclic peptides as well as some of their artificial derivatives and analogs possessing desirable pharmacological properties have been synthesized. However, wider medical use is often hampered due to complexity of their synthesis and purification. Therefore, improved methods for making these compounds in simple, lesser steps and at lesser cost are desirable and this is the felt need of the industry and the mankind.

Conventional synthesis of octreotide may be divided into two main approaches, direct solid-phase synthesis and liquid-phase synthesis. Solution phase synthesis has been described by Bauer et al., (Sandoz) (Eur. Pat. Appl. 29,579 and U.S. Pat. No. 4,395,403). The process comprises: removing protected group from peptide; linking together by an amide bond two peptide unit; converting a function group at the N- or C-terminal; oxidizing a straight chain polypeptide by boron tris-trifluoroacetate. This process involves a time-consuming, multi-step synthesis, and it is difficult to separate octreotide from the reaction mixtures since all the synthesis steps are carried out in liquid phase. Another solution phase approach described by Chaturvedi, et al., (Wockhardt) in U.S. Pat. No. 6,987,167 and EP 1506219 A, claims the cyclization of partially deprotected octreotide in the solution phase using iodine under conditions and for a time sufficient to form the octreotide.

Synthesis in solid phase have been described subsequently (Mergler et al., Alsina et al., Neugebauer). The above prior art for solid phase peptide synthesis cites the octapeptide formation, by starting the synthesis from the threoninol residue which makes it mandatory to protect this residue. Mergler et al., (Peptides: Chemistry and Biology. Proceedings of the 12$^{th}$ American Peptide Symposium. Smith, J. A. And Rivier J. E. Eds ESCOM, Leiden, Poster 292 Presentation, (1991)) describes a synthetic process, using an aminoethyl resin upon which the Threoninol residue is incorporated with the two alcohol functions protected in acetal form The synthesis is carried out following an Fmoc/tBu protection scheme, forming the disulphide bridge on resin by oxidation of the thiol groups of the previously deprotected cysteine residues and releasing and deprotecting the peptide with a 20% mixture of TFA/DCM.

In early 1997, Alsina J. et al. (Alsina J., Chiva C., Ortiz M., Rabanal F., Giralt E., and Albericio F., Tetrahedron Letters, 38, 883-886, 1997) described the incorporation, on active carbonate resins, of a Threoninol residue with the amino group protected by the Boc group and the side chain protected by a Bzl group. The synthesis was then continued by Boc/Bzl strategy. Formation of the disulfide bridge was carried out directly on resin using iodine and the peptide was cleaved from the resin and its side chain protecting groups were simultaneously removed with HF/anisole 9/1. At the final stage the formyl group was removed with a piperidine/DMF solution.

Neugebauer (Neugebauer W., Lefevre M. R., Laprise R, Escher E., Peptides: Chemistry, Structure and Biology, p 1017, Marshal G. R. And Rivier J. E. Eds. ESCOM.Leiden (1990) described a linear synthesis with a yield of only 7%.

Edwards et al., (Edwards B. W., Fields C. G., Anderson C. J., Pajeau T. S., Welch M. J., Fields G. B., J. Med. Chem. 37, 3749-3757 (1994) carried out another another solid-phase type approximation; they synthesized step-by-step on the resin, the peptide D-Phe-Cys(Acm)-Phe-D-Trp(Boc)-Lys(Boc)-Thr(tBu)-Cys(Acm)-HMP-Resin. Next they proceeded to form the disulfide on resin and then release the peptide from the resin by means of aminolysis with threoninol, with obtaining a total yield of only 14%.

The solid phase synthesis described by Yao-Tsung Hsieh et. al., in U.S. Pat. No. 6,476,186 involves the synthesis of octreotide by using Thr(ol)(tBu)-2Cl-trityl resin as starting material followed by the cleavage of the straight chain peptide from the resin by using a strong acid and the formation of the intra-molecular disulfide bond on the completely deprotected octreotide by oxidation using charcoal catalyst and a higher yield of >70%.

Another solid phase synthesis described by Berta Ponsati et.al (Lipotec) in U.S. Pat No. 6,346,601 and EP 0953577 B involve the coupling of threoninol on the protected heptapeptide in solution, after a selective acid cleavage from the chlorotrityl resin without affecting the peptide side-chain protecting groups.

A hybrid solid phase-liquid phase method for synthesis of octreotide described by Iarov et al., (Dalton Chemical Laboratories) in WO 2005087794 wherein the method comprises liquid phase condensation of two or three peptide blocks in which at least one peptide block is synthesized by solid-phase method.

EP 1511761 B1 involves cyclization on the semi-protected linear peptide wherein one of the cysteine residues is protected with an orthogonal protecting group.

The radioactive isotope labeling of octreotide by the coupling of bifunctional chelating agents like DTPA or DOTA to the peptide was described by Te-Wei Lee et al., in U.S. Pat. No. 5,889,146 (Inst. of Nuclear Energy Research)

The method for cyclization of linear vapreotide by means of intramolecular cysteine formation has been described by Quattrini et. al., (Lonza AG) in WO 2006048144, wherein the process involves the synthesis of linear vapreotide peptide on Sieber-resin (from Novabiochem) by Fmoc standard groups, wherein the side chain protecting groups are D or L-Trp(Boc), Cys(Trt), Lys(Boc), Tyr(tBu). The protected peptide is cleaved off in 5% TFA in dichloromethane and then globally deprotected by acidolysis in a cleavage mix of 300 equivalents of concentrated TFA, 12 equivalents of Dithiothreitol, 12 equivalents of Dichloromethane, 50 equivalents of water for 1 hour at room temperature. The Boc groups are removed. The product was subjected to charcoal method using trace amounts of activated, powdered charcoal wherein a concentration of the linear cysteinyl peptide of 50 mg/ml (1 eq.) in DMF in the presence of 1 eq. Diisopropyl-ethyl-amine and that additionally air was sparged at low pressure into the liquid under stirring. After 15-20 hrs, 100% conversion was achieved with 84% (w/w) analytical yield of 79% vapreotide.

The formation of intramolecular disulphide formation in a polypeptide by reacting with hydrogen peroxide has been described by Mineo Niwa et al. (Fujisawa Pharmaceutical Co.) in U.S. Pat. No. 5,102,985 wherein the reaction is to be carried out at a pH of about 6 to 11, wherein the molar ratio of $H_2O_2$ to polypeptide is within the range of 1:1 to 100:1.

The above cited prior art mainly carries out the cyclization of the peptide on the resin or on partially protected or protected peptides. The use of partial or minimal protecting group strategies and improvement in the activation methods have considerable effect on limitations of poor solubility and possible danger of racemization due to the overactivation of carboxyl groups. However, these approaches do not overcome the problem of the poor coupling efficiency between large peptide segments, because of the intrinsic difficulty of obtaining effective molar concentrations for high molecular weight molecules.

OBJECT OF INVENTION

The main object of the present invention is to provide a novel process for synthesis of octreotide and derivatives thereof wherein the process uses mild reagents, isolates protected peptide by simple aqueous precipitation, avoids usage of hazardous thiol scavengers in the cleavage cocktail, achieves effective oxidation of deprotected peptide in the presence of hydrogen peroxde to yield a clean crude cyclic octapeptide at a purity of >70% with an overall yield of 95%.

Another object of the present invention is to obtain pure octreotide with a purity of >99% with total impurity <1%.

Still another object of the invention is an improved process for cyclization of octreotide wherein the cyclization is carried out in the presence of hydrogen peroxide on a completely deprotected heptapeptide or octapeptide.

SUMMARY OF INVENTION

One embodiment of the present invention is an improved process for preparing octreotide of formula

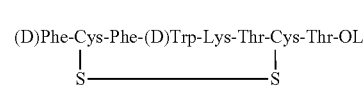

Formula (1)

comprising the following steps:

i. using H-Cys (Trt)-2-chlorotrityl resin as the starting material, coupling of various selected amino acid residues using coupling agent in polar aprotic solvent to give the straight chain peptide resin compound of formula 2 Boc-D-Phe-Cys(Trt)-Phe-D-Trp-Lys(Boc)-Thr(OBut)-Cys(Trt)-2-Chlorotrityl resin;

ii. cleaving the product of step i with a solution comprising of TFA in dichloromethane or acetic acid in dichloromethane to give straight chain peptide of formula 3 Boc-D-Phe-Cys(Trt)-Phe-D-Trp-Lys(Boc)-Thr(OBut)-Cys(Trt)-OH;

iii. coupling of threoninol to the C-terminal in the presence of benzotriazole to give linear protected octapeptide of the formula 4 Boc-D-Phe-Cys(Trt)-Phe-D-Trp-Lys(Boc)-Thr(OBut)-Cys(Trt)-Thr-OL;

iv. deprotecting the product of step iii with TFA, triisopropylsilane and water to give linear deprotected octapeptide of formula 5

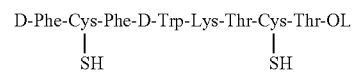

v. oxidizing the deprotected octapeptide of step iv at an acidic pH in the range of 2.5 to 6.5 in the presence of hydrogen peroxide to yield octreotide of formula 1;

vi. purifying the crude octreotide of step v by chromatography to a purity of ≧99%;

vii. converting the pure octreotide of step vi to acetate salt;

viii. concentrating the acetate salt of octreotide of step vii and lyophilizing the same.

Second embodiment of the present invention is a process for preparing octreotide of formula

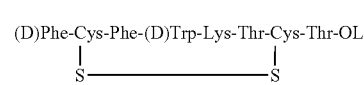

Formula (1)

comprising the following steps:

i. using H-Cys (Trt)-2-chlorotrityl resin as the starting material, coupling of various selected amino acid residues using coupling agent in polar aprotic solvent to give the straight chain peptide resin compound of formula 2 Boc-D-Phe-Cys(Trt)-Phe-D-Trp-Lys(Boc)-Thr(OBut)-Cys(Trt)-2-Chlorotrityl resin;

ii. cleaving the product of step i with a solution comprising of TFA in dichloromethane or acetic acid in dichloromethane to give straight chain peptide of formula 3 Boc-D-Phe-Cys(Trt)-Phe-D-Trp-Lys(Boc)-Thr(OBut)-Cys(Trt)-OH;

iii. deprotecting the product of step ii with TFA, triisopropylsilane and water to give linear deprotected heptapeptide of formula 6

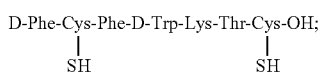

Formula 6 iv. oxidizing the deprotected heptapeptide of step iii at an acidic pH in the range of 2.5 to 6.5 in the presence of hydrogen peroxide to yield heptapeptide of formula 7

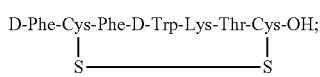

Formula 7 v. coupling of threoninol to the C-terminal in the presence of benzotriazole to yield octreotide of the formula 1;
vi. purifying the crude octreotide of step v by chromatography to a purity of ≧99%;
vii. converting the pure octreotide of step vi to acetate salt;
viii. concentrating the acetate salt of octreotide of step vii and lyophilizing the same.

Third embodiment of the present invention is Octreotide of formula 1 as claimed, wherein the purification of the crude cyclic octapeptide to a purity of ≧99% is carried by ion exchange chromatography followed by RP-HPLC in gradient mode.

Fourth embodiment of the present invention is a pharmaceutical composition comprising octreotide of formula I as claimed and at least one pharmaceutically acceptable excipient.

BRIEF DESCRIPTION OF ACCOMPANYING DRAWINGS

Figure 2:
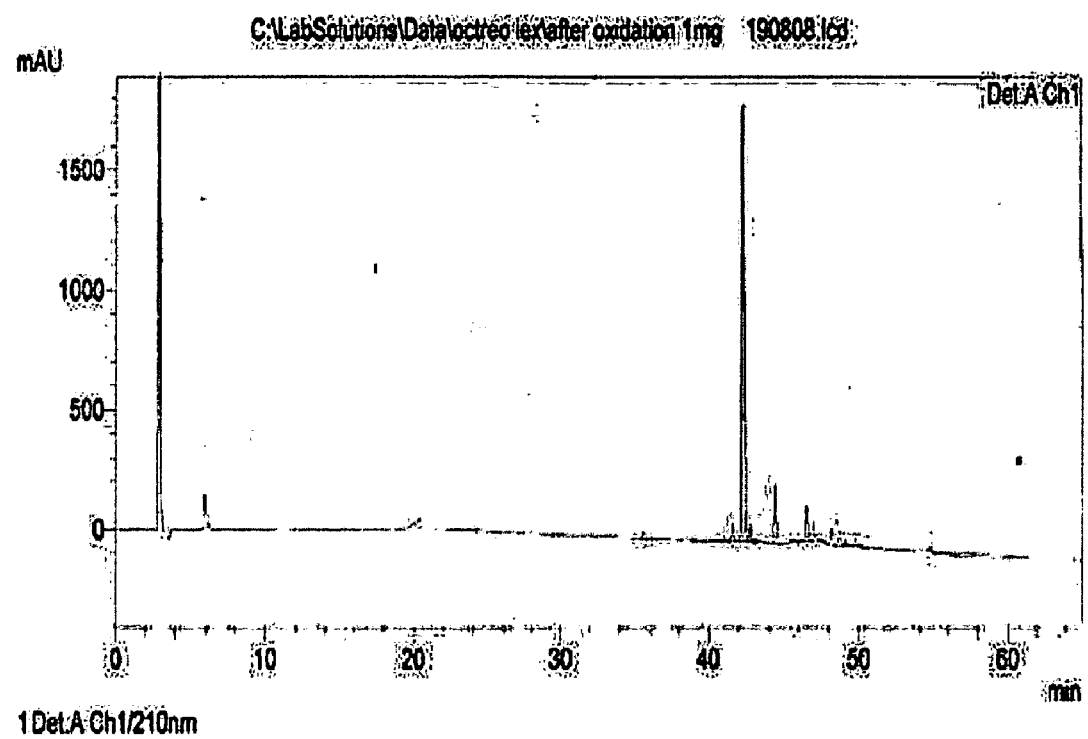
Figure 3:
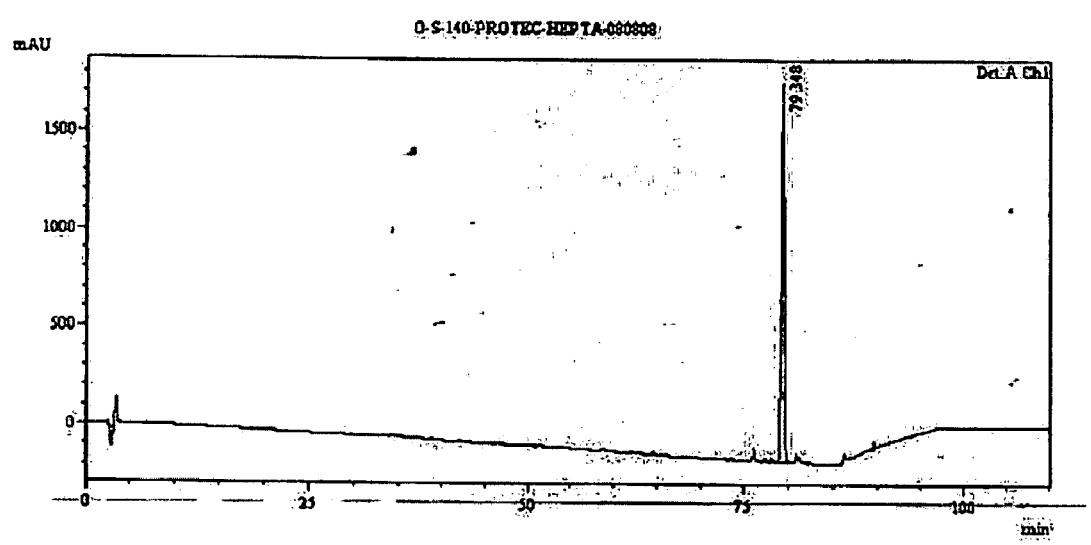
Figure 4:
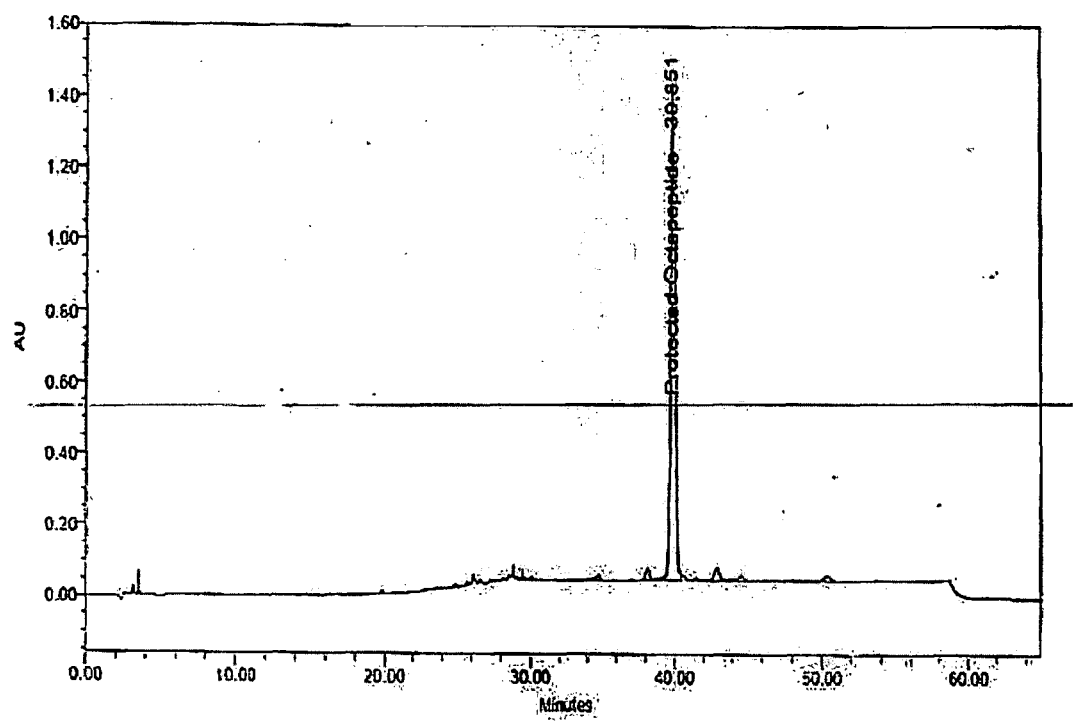
Figure 5:
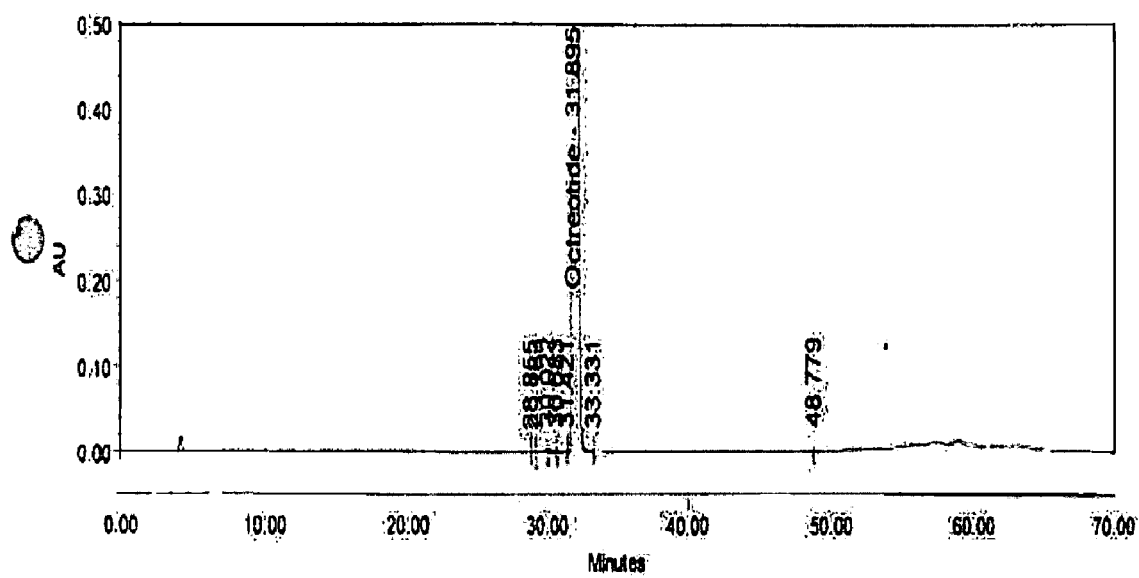
Figure 6:
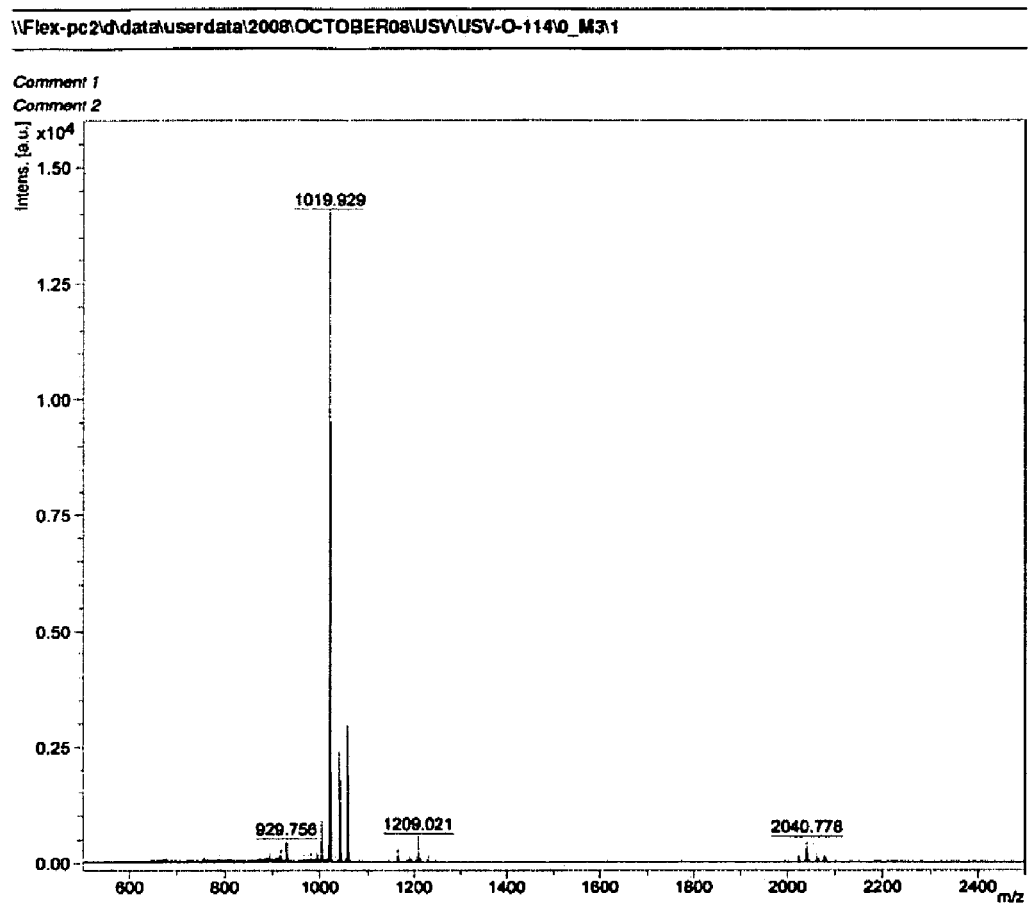

The manner in which the objects and advantages of the invention may be obtained will appear more fully from the detailed description and accompanying drawings, which are as follows:

FIG. 1: RP-HPLC profile of crude octreotide using DMSO for oxidation of S—H to S—S.
FIG. 2: RP-HPLC profile of crude octreotide using H2O2 for oxidation of S—H to S—S.
FIG. 3: RP-HPLC profile of linear protected heptapeptide at 210 nm wavelength.
FIG. 4: RP-HPLC profile of protected octapeptide.
FIG. 5: RP-HPLC purity profile of pure octreotide.
FIG. 6: MS spectrum of pure octreotide with a mass of 1019.9 Da.

DETAILED DESCRIPTION OF THE INVENTION

Synthesis of peptides on a solid support is a conventional method which has known advantages cited in the prior art. Impurities found with the desired peptide are derived from three sources: namely, coupling of amino acid derivatives to the growing peptide chain, cleavage of the peptide from the solid support, and deprotection of side-chains of the assembled sequence. Impurities often have small differences in structure such as the deletion of one amino acid residue resulting from a slow coupling reaction or a rearranged/derivatized side-chain group formed during the cleavage of the peptide from the solid support. However, in addition to maintaining the purity of the peptide, a major challenge also is to substantially increase the yield or recovery of the peptide synthesized. Complexity increases with the synthesis of cyclic peptides. The preparation of cyclic peptide disulfides from the corresponding SH-precursors and the direct conversion of the cysteine-protected derivatives into cyclic products (deprotection of the -SH groups with simultaneous cyclization) are most widely used among the diversity of methods known for the synthesis of disulfide containing peptides. As a rule, in both cases, the cyclization is carried out in very dilute solutions, with the peptide concentration being of $10^{-4}$-$10^{-5}$ M in order to avoid an intermolecular aggregation and side reactions. The directed formation of S—S bonds in the highly diluted solutions significantly depends on structural peculiarities of a peptide, in particular, on the nature of amino acid residues between Cys residues. The cyclization of free thiols by the air oxygen usually leads to low yields of target products (9-15%). In the air-oxidation process, the proceeding speed of the reaction progress itself is very slow, and especially, it hardly proceeds under denaturing condition, such as in a highly concentrated salt or urea-aqueous solution of polypeptide. The application of potassium ferricyanide or dimethyl sulfoxide usually result in homogeneous reaction mixtures and the yields of cyclic products are considerably higher (from 20 to 60%, and, in some cases, up to 80%, which depends on the peptide structure). However, a multistage purification of product is necessary for the removal of excess of these oxidative agents. Moreover it produces the problem of environmental pollution, since the resultant waste water contains $CN^-$. A very attractive one-step formation of the disulfide bridges by the action of iodine is often accompanied by side reactions and has only a limited use in the case of Trp- and Met-containing peptides. In the iodine-oxidation process, tyrosine residues in a peptide may be disadvantageously iodinated.

An inherent feature of the present invention is provision of sufficiently homogenous reaction mixture and a simple, preferably one step isolation of octapeptide of >70% purity which on subsequent chromatographic purification yields an octapeptide of >99% purity. More particularly the oxidation process is easily upscaled and is least cost intensive relatively lowering the manufacturing cost.

Producing cyclized peptides with the correct structure can be achieved readily by either on-resin or post-cleavage techniques. On-resin techniques produce greater yields of the final products, but are more expensive to perform. However, post-cleavage techniques are less expensive and provide reasonable yields of the desired product. Another feature of the present invention is post-cleavage cyclization of the heptapeptide and subsequent coupling of threoninol or direct cyclization of the octapeptide to form cyclic octapeptide.

The solid-phase synthesis of octreotide had several potential pitfalls that could reduce peptide assembly and cleavage efficiencies and/or resulted in deletereous side reactions. Potential problems included i) racemization of the C-terminal Cys residue, ii) inefficient disulfide bond formation on resin, iii) modification of Trp during disulfide bond formation, and iv) incomplete peptide-resin cleavage. Racemization during the esterification of the C-terminal amino acid or during the chain elongation is suppressed by several alternative techniques. One of the essential feature of the present invention wherein C-terminal Cys peptide is successfully synthesized without racemization by Fmoc based solid phase method using 2-chlorotrityl resin. The use of 2-Chlorotrityl resin circumvents the racemization at the C-terminal cysteine caused by the base treatment, probably due to its high steric hindrance. Another novel feature of the present invention is cyclization of the fully deprotected heptapeptide or octapeptide.

Iodine, however, is not without drawbacks as a cyclization agent. For instance, tryptophan moieties present in peptide substrates are at risk of being modified, making the balance between full conversion of starting materials and minimizing side reactions a delicate one, which, in turn, impacts product purity. In the present invention this aspect has been rightfully tackled by not opting for Iodine route for oxidative cyclization. Therefore the process of the present invention has a product of enhanced purity and better yield. Another complicating factor in known synthesis routes is the possibility of interaction between the desired cyclic disulfide and inorganic sulfur compounds used for reducing excess iodine at the end of the reaction, such as sodium dithionite or sodium thiosulfate. Such reducing sulfur-containing compounds may interact with the disulfide linkage, which is sensitive to nucleophilic attack in general. As the process of the present invention does not use iodine, the resulting products have high purity and related impurities are undetectable.

The solution phase route is more cumbersome as after each coupling the peptide has to be isolated, as compare to the solid phase route where the excess reagents and by-products are washed off by simple filtration. In both, the desired peptide compound is created by the step-wise addition of amino acid moieties to a growing peptide chain. As compared to Boc-chemistry, Fmoc-chemistry based synthesis is a mild procedure and because of the base liability of Fmoc group, acid-labile side-chain protecting groups are employed giving an orthogonal protection strategy. The rationale for use of protecting groups is that the energy of breaking a bond of a protecting group is lower than any other group in question. Where appropriate, these are based on the tert-butyl moiety: tert-butyl ethers for Ser, Thr, tert-butyl esters for Asp, Glu and Boc for Lys, His. The trt group has been extensively used for the protection of Cys. Also for Cys, the Acm group is extensively used when a protecting group on the sulfur needs to be maintained after the cleavage of the peptide. The guanidine group of Arg is protected by Mtr, Pmc or Pbf. Most Of the Fmoc-amino acids derivatives are commercially available. However, a problem exists in the art for the preparation of modified amino acid peptides as well as cyclic peptide compounds based on disulfide links because separate operations are required before purifying the end product, which increases expense and may effect final product quality and quantity.

The purity of a peptide has several aspects. One is purity on the basis of an active-compound concentration scale. This is represented by the relative content of the pharmacologically active compound in the final product, which should be as high as possible. Another aspect is the degree of absence of pharmacologically active impurities, which though present in trace amounts only, may disturb or even render useless the beneficial action of the peptide when used as a therapeutic. In a pharmacological context both aspects have to be considered. As a rule, purification becomes increasingly difficult with larger peptide molecules. In homogeneous phase synthesis (which is the current method of choice for industrial production of larger amounts of peptides) repeated purification required between individual steps provides a purer product but low yield. Thus, improvements in yield and purification techniques at the terminal stages of synthesis are needed. The present invention is an industrially feasible solid phase synthesis and is a novel process to yield a high purity product with greater yields.

A general outline for the synthesis of octreotide in the present invention is described as follows: The heptapeptide is synthesized as peptide acid by solid phase peptide synthesis technology on 2-Chloro Trityl chloride Resin using Fmoc chemistry.

Instrument: CS936, CS BIO, California; Peptide synthesizer.
Resin: H-Cys(Trt)-2Cl Trityl Resin.
Activator: HBTU/NMM
Solvent: Dimethyl Formamide
Deprotection 20% Piperidine in DMF a) The resin H-Cys(Trt)-2Cl Trityl Resin, 10 mmole is transferred to the RV of the CS936 & the linear peptide assembled on it using 1.5-4 times mole excess amino acid derivatives, on the peptide synthesizer. Each coupling is carried out for a time range of 45-90 min. After the couplings are complete, resin is washed with DMF (60-100 ml three washings) followed by 0.2% DIPEA in DCM (60-100 ml six washings) & dried under vacuum. The details of the synthesis are described in the examples.
b) cleavage of the peptide from the resin using the cocktail mixture consisting of TFA in DCM or Acetic acid in DCM
c) coupling of peptide in formula 3, with Threoninol to give protected octa-peptide of formula 4.
d) isolation of peptide post Threoninol coupling by precipitation with water.
e) isolation of peptide in step C can also be done by chromatography.
f) removal of protecting group by using TFA cocktail mixture from formula 4 followed by oxidation with $H_2O_2$, to give peptide of formula 1. The crude peptide is purified by chromatography.

The abbreviations used in this description have the meanings set forth below:

| | Glossary |
|---|---|
| AA | Amino Acid |
| ACT | Activator |
| Arg | Arginine |
| Asp | Aspartic Acid |
| Boc | Tert-butyloxycarbonyl |
| Cys | Cysteine |
| DCM | Dichloromethane |
| DEP | Deprotection reagent |
| DMF | Dimethyl Formamide |
| DIPEA | N,N-diisopropylethylamine |
| DMSO | Dimethyl slphoxide |
| Fmoc | 9-fluorenylmethyloxycarbonyl |
| Glu | Glutamic acid |
| Gly | Glycine |
| HBTU | 2-(1H-Benzotriazole1-yl)-1,1,3,3-tetramethyluronium hexafluorophosphate |
| HF | Hydrogen Fluoride |
| HIC | Hydrophobic Interaction Chromatography |
| His | Histidine |
| IEC | Ion Exchange Chromatography |
| LC-MS | Liquid Chromatography-Mass Spectroscopy |
| Lys | Lysine |
| Mtr | 4-methoxy-2,3,6-trimethylbenzenesulfonyl |
| MeOH | Methanol |
| NMM | N-methyl morpholine |
| Obut | O-t-butyl |
| Pbf | 2,2,4,6,7-pentamethyldihydrobenzofuran-5-sulfonyl |
| Phe | Phenyl alanine |
| Pmc | 2,2,5,7,8-pentamethylchroman-6-sulfonyl |
| Pro | Proline |
| RP-HPLC | Reverse Phase High Performance Liquid Chromatography. |
| RV | Reaction Vessel |

-continued

| | Glossary |
|---|---|
| Ser | Serine |
| SOLV | Solvent |
| SP | Synthetic Peptide |
| TEA | Triethylamine |
| TFA | Trifluoroacetic acid |
| Thr | Threonine |
| TIS | Triisopropylsilane |
| Trp | Tryptophan |
| Trt | Trityl |

EXAMPLES

Example 1

Attachment of First Amino Acid Cys(Trt) to 2-Chlorotrityl Chloride Resin to give H-Cys(Trt)-2-Chlorotrityl resin:

Fmoc-Cys(Trt)-OH (52.6 gm, 90 mmol) was suspended in 500 ml dichloromethane. DIPEA (47.12 ml, 270 mmoles) was added to it. The mixture was stirred for 10 minutes. While under stirring, 2-ChloroTrityl chloride resin(1.13 mmoles/gm, 22.73 g; 30 mmole) was added. The resulting mixture was continuously stirred for one hour under nitrogen atmosphere. The resin was filtered and washed with DMF (80 ml×6 washings for 3 min) followed by 0.2% DIPEA in DCM (60 ml-100 ml×6 washing for 5 min).

The resin was capped with MeOH:DCM:DIPEA 200 ml×3, for 5 min each after swelling in DCM. The resin was swelled again in DMF. 20% piperidine in DMF (100 ml×3) was used for deprotection (Fmoc removal) for 5 minutes each. The resin was washed with DMF (60 ml-100 ml×6) for 3 minutes each. The resin was washed with 0.2% DIPEA in DCM (100 ml×3 times) for 3 minutes each time. The resin was dried for 12-15 hours under high vacuum.

Yield >90% Substitution: 0.6 mmoles/gm.

Example 2

Chemical Synthesis of Protected (1-7) Fragment of Octreotide (heptapeptide):

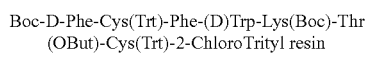
Boc-D-Phe-Cys(Trt)-Phe-(D)Trp-Lys(Boc)-Thr (OBut)-Cys(Trt)-2-ChloroTrityl resin    Formula 2

The peptide was synthesized as peptide acid by solid phase peptide synthesis technology on H-Cys(Trt)-2-chlorotrityl resin using Fmoc chemistry.

| Instrument | CS-BIO-936, |
|---|---|
| Resin | Peptide synthesizer H-Cys(Trt)-2-ChloroTrityl resin (0.6 mmoles/gm). |
| Side chain protecting groups | Thr: OBut; Cys: Trt; Lys: Boc. |
| Activator | HBTU/NMM |
| Solvent | Dimethyl Formamide. |

The H-Cys(Trt)-2-Chlorotrityl resin (16.666 g, 10 mmole) was transferred into the RV of the CS 936. The assembly of the remaining amino acids was carried out using side chain protected Fmoc derivatives of Thr, Lys, (D)Trp, Phe, Cys, and BOC protected (D)Phe with HBTU (2 times excess; 20 mmole) on the peptide synthesizer. Each coupling was carried out for 60 minutes. The completion of coupling was monitored by Kaiser test, which indicated the completeness of coupling reaction (>99%), when negative. After the couplings were complete, resin was washed with 0.2% DIPEA in DCM (100 ml×6) and product was dried under high vacuum over drying agents like calcium chloride.

Yield: >90%.

Example 3

Cleavage of Protected Heptapeptide Fragment of Octreotide:

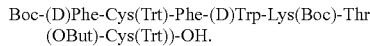
Boc-(D)Phe-Cys(Trt)-Phe-(D)Trp-Lys(Boc)-Thr (OBut)-Cys(Trt))-OH.    Formula 3

The dried peptidyl-resin(40 gm) was treated with 500 ml of 0.1% TFA v/v in dichloromethane for 5 minutes and filtered. The process was repeated for six times. The filtrate was concentrated under vacuum on rotavap & cold ether was added (300 ml) to precipitate the protected heptapeptide. The precipitate was triturated with spatula and kept in cold followed by filteration through G-4 sintered funnel. The precipitate was washed with 100 ml of ether twice and dried under vacuum. The RP-HPLC profile of linear protected heptapeptide is depicted in FIG. 3.

Yield: >95%
Purity by RP-HPLC=88.64%

Example 4

Deprotection of Protected Heptapeptide, to get SH-heptapeptide:

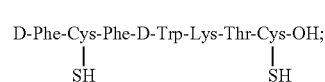

D-Phe-Cys-Phe-D-Trp-Lys-Thr-Cys-OH;    Formula 6
       |                           |
      SH                          SH Cleavage cocktail mixture TFA:TIS:WATER (95:2.5:2.5) was prepared & kept at 4° C. 60 ml of cocktail was added to protected-heptapeptide (3 gm) slowly under stirring and nitrogen atmosphere. Stirring was continued for 2 hours and 45 minutes.

The reaction mixture was concentrated. To the concentrate, cold DIPE (600 ml) was added to precipitate the crude ACM-heptapeptide & kept at −20° C. overnight. The precipitate was filtered, followed by DIPE wash and the precipitate dried under vacuum for 18 hours at room temperature.

Oxidation of heptapeptide using H2O2:

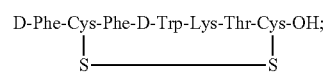

D-Phe-Cys-Phe-D-Trp-Lys-Thr-Cys-OH;    Formula 7
       |                           |
       S———————————————————S The heptapeptide was oxidised to form disulfide as in Example 7.

Coupling of Threoninol to the deprotected disulfide heptapeptide:

The deprotected disulfide heptapeptide (300 mg w/w, 0.259 mmole) was dissolved in hydroxy benzotriazole (159 mg, 1.036 mmole), in dimethylacetamide (1 ml) followed by addition of & threoninol (108 mg, 1.036 mmole). The reaction mixture was cooled to 15° C. DCC(60 mg, 0.285 mmole) solution (0.2 ml) was added to the reaction mixture and stirred at 15° C. for 1 hour. Additional stirring was carried out at room temperature for 60 hours. The reaction was monitrored by HPLC. After 20 hours, 70% of the reaction was completed. Further monitored coupling after 60 hours, 85 to 90% of the coupling was completed. The peptide was precipitated from reaction mixture by addition of 40 ml of ethyl acetate followed by stirring at room for 2 hours. The product was filtered on whatman filter paper and dried under vacuum for 20 hours.

Purity: 50%

Example 5

Coupling of Threoninol to Protected Heptapeptide to Give Protected Octapeptide:

Boc-(D)Phe-Cys(Trt)-Phe-(D)Trp-Lys(Boc)-Thr(OBut)-Cys(Trt))-Thr-OL.   Formula 4

The protected heptapeptide (24 gm) and hydroxy benzotriazole (6.26 gm) was dissolved in dimethylacetamide (100 ml) followed by addition of threoninol (4.2 gm). The reaction mixture was cooled to 15° C.-20° C. DCC (3.069 gm) was added to the reaction mixture and stirred at 15° C. for 1 hour. Additional stirring was carried out at room temperature for 24 to 72 hours. After the reaction was completed, the urea was filtered on sinter funnel. The urea was washed with 5 ml of DMAC twice. The filtrate fractions were pooled and dropwise added to 0.5% solution of sodium bicarbonate in 1 L of water under stirring at 20° C., further after 15 minutes 500 ml of water was added at 20° C. The stirring was continued for another 1 hour. The precipitate was filtered and washed with 100 ml of water five times. The RP-HPLC profile of linear protected octapeptide is depicted in FIG. 4.

Dried under vacuum for 30 hours
Yield: >95%
Purity by RP-HPLC=81.38%

Example 6

Deprotection of Protected Octapeptide to Give SH-Octapeptide:

(D)Phe-Cys-Phe-(D)Trp-Lys-Thr-Cys-Thr-OL.   Formula(5)
   |                          |
   SH                         SH The protected octapeptide (23 gm) was treated with TFA/TIS/Water (1150 ml) for 2 hours and 45 minutes for the removal of side chain protecting groups. TFA was evaporated, and peptide precipitated by addition of cold DIPE(500 ml). The solution was filtered and washed with DIPE(100 ml×3) and the precipitate dried.

Yield: >95%

Example 7

Hydrogen Peroxide Oxidation of S—H Octapeptide:

┌──────────────────────┐
   (D)Phe-Cys-Phe-(D)Trp-Lys-Thr-Cys-Thr-OL   Formula (1)

S—H Octapeptide(15 gm) was dissolved in water at a concentration of 2 mg/ml and pH adjusted to 6.5 to 7 with ammonium hydroxide solution. Hydrogen peroxide solution (450 ml) was added in three parts over a period of half hour and allowed to stir at RT over a period of one hour and then acidified to pH <3 with acetic acid. The crude disulfide looped peptide was filtered and solution was taken for IEC purification. The purity was estimated by RP-HPLC (FIG. 2).

Purity: 70.5%

Example 8

Oxidation of S—H Peptide with DMSO-HCl to Get S—S Peptide:

┌──────────────────────┐
   (D)Phe-Cys-Phe-(D)Trp-Lys-Thr-Cys-Thr-OL   Formula (1)

S—H peptide (9 g) was dissolved in 6.5 L DMSO and under ice-cooling 6.5 L 1M HCl was added slowly so that temperature is below 26° C. Stirring was continued for 6 hours. At room temperature after six hours reaction mixture was diluted with 13 L of water and filtered through Whatman no. 41 through Celite bed. The filtrate was loaded on C-18 column for concentration. The compound was eluted with 100% acetonitrile. The eluant was concentrated on rotavap and then the concentrated solution was centri-evaporated to dryness. The RP-HPLC profile of crude octreotide is depicted in FIG. 1.

Weight of crude peptide=3.9g.(45%)
Purity: 44.25%

Example 9

Purification of Crude Octreotide:

The crude octreotide was loaded on to cation ion exchange column and eluted using a salt gradient using a Akta Purifier (by Amersham, Sweden) low pressure chromatography system. The IEX fractions of purity >70% were further loaded for RP-HPLC purification on Kromacil C-18 column of (250×50 mm, 100 A°.) The peptide was purified by using aqueous TFA(0-0.5%) and methanol/ethanol and/or Acetonitrile in a gradient program on a Shimadzu preparative HPLC System consisting of a controller, 2 LC8A pumps, and UV-Vis detector. The purified peptide was analysed by analytical RP-HPLC (FIG. 5). Fractions of >99% purity were subjected either by RP-HPLC or IEX to salt exchange and concentrated to remove organic solvent either by rota or reverse osmosis and subsequently lyophilized to get final API with purification step yield of 70% or above. The MS spectrum of octreotide is depicted in FIG. 6.

The above discussed sequences disclosed throughout this specification have the following sequence listings:

```
SEQ. ID NO. 1 (also known as Formula 1):
       (D)Phe-Cys-Phe-D)Trp-Lys-Thr-Cys-Thr-OL
            |                    |
            S────────────────────S
```

-continued

```
SEQ. ID NO. 2 (also known as Formula 2):
         Boc-D-Phe-Cys(Trt)-Phe-D-Trp-Lys(Boc)-Thr(OBut)-Cys(Trt)-2-Chlorotrityl
SEQ. ID NO. 3 (also known as Formula 3):
         Boc-D-Phe-Cys(Trt)-Phe-D-Trp-Lys(Boc)-Thr(OBut)-Cys(Trt)-OH
SEQ. ID NO. 4 (also known as Formula 4):
         Boc-D-Phe-Cys(Trt)-Phe-D-Trp-Lys(Boc)-Thr(OBut)-Cys(Trt)-OL
SEQ. ID NO. 5 (also known as Formula 5):
         D-Phe-Cys-Phe-D-Trp-Lys-Thr-Cys-Thr-OL
```
```
SEQ. ID NO. 6 (also known as Formula 6):
         D-Phe-Cys-Phe-D-Trp-Lys-Thr-Cys-OH
```
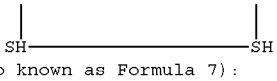
```
SEQ. ID NO. 7 (also known as Formula 7):
         D-Phe-Cys-Phe-D-Trp-Lys-Thr-Cys-OH
```
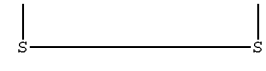

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

We claim:

1. A process for preparing octreotide of formula

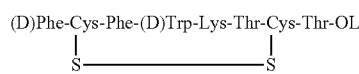

Formula (1)

comprising the following steps:

i) using H-Cys (Trt)-2-chlorotrityl resin as the starting material, coupling of various selected amino acid residues using coupling agent in polar aprotic solvent to give the straight chain peptide resin compound of formula 2

Boc-D-Phe-Cys(Trt)-Phe-D-Trp-Lys(Boc)-Thr(OBut)-Cys(Trt)-2-Chlorotrityl resin;

ii) cleaving the product of step i with a solution comprising of TFA in dichloromethane or acetic acid in dichloromethane to give straight chain peptide of formula 3

Boc-D-Phe-Cys(Trt)-Phe-D-Trp-Lys(Boc)-Thr(OBut)-Cys(Trt)-OH;

iii) coupling of threoninol to the C-terminal in the presence of benzotriazole to give linear protected octapeptide of the formula 4

Boc-D-Phe-Cys(Trt)-Phe-D-Trp-Lys(Boc)-Thr(OBut)-Cys(Trt)-Thr-OL;

iv) deprotecting the product of step iii with TFA, triisopropylsilane and water to give linear deprotected octapeptide with a yield >95% of formula 5

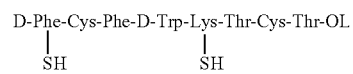

v) oxidizing the deprotected octapeptide of step iv at an acidic pH in the range of 2.5 to 6.5 in the presence of hydrogen peroxide to yield octreotide of formula 1;

vi) purifying the crude octreotide of step v by chromatography to a purity of >99%;

vii) converting the pure octreotide of step vi to acetate salt;

viii) concentrating the acetate salt of octreotide of step vii and lyophilizing the same.

2. A process for preparing octreotide of formula

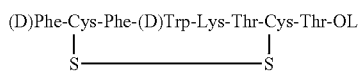
Formula (1)

comprising the following steps:
i) using H-Cys (Trt)-2-chlorotrityl resin as the starting material, coupling of various selected amino acid residues using coupling agent in polar aprotic solvent to give the straight chain peptide resin compound of formula 2

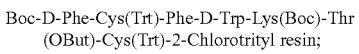

ii) cleaving the product of step i with a solution comprising of TFA in dichloromethane or acetic acid in dichloromethane to give straight chain peptide of formula 3

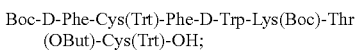

iii) deprotecting the product of step ii with TFA, triisopropylsilane and water to give linear deprotected heptapeptide of formula 6

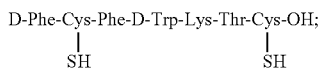
Formula 6 iv) oxidizing the deprotected heptapeptide of step iii at an acidic pH in the range of 2.5 to 6.5 in the presence of hydrogen peroxide to yield >95% heptapeptide of formula 7

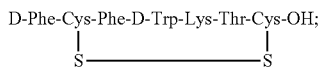
Formula 7 v) coupling of threoninol to the C-terminal in the presence of benzotriazole to yield octreotide of the formula 1;
vi) purifying the crude octreotide of step v by chromatography to a purity of ≧99%;
vii) converting the pure octreotide of step vi to acetate salt;
viii) concentrating the acetate salt of octreotide of step vii and lyophilizing the same.

3. The process as claimed in claim 1 or claim 2, wherein the coupling agent used is HBTU.

4. The process as claimed in claim 1 or claim 2, wherein the N-α $NH_2$ protected amino acids are added in 1.5 to 5 molar excess for synthesis of said octapeptide.

5. The process as claimed in claim 1 or claim 2, wherein the deprotectant is piperidine.

6. The process as claimed in claim 1 or claim 2, wherein said cleavage cocktail consists of 0.1% TFA v/v in dichloromethane to yield linear protected heptapeptide of formula 3 with a purity of ≧85%.

7. The process as claimed in claim 1, wherein the threoninol coupling is carried out in dimethylacetamide and by addition of 1,3-dicyclohexylcarbodiimide.

8. The process as claimed in claim 1, wherein the isolation of linear protected octapeptide of formula 4 is carried out by precipitation with water.

9. The process as claimed in claim 1 or claim 2, wherein the purification of the crude octreotide of Formula 1 to a purity of ≧99% is carried by ion exchange chromatography followed by RP-HPLC in gradient mode.

10. The process as claimed in claim 9, wherein the RP-HPLC elution is carried out by using ethanol.

11. The process as claimed in claims 1 or 2, wherein the polar aprotic solvent is selected from the group consisting of DMF, THF and DCM.

12. The process as claimed in claim 11 wherein the polar aprotic solvent is DCM.

13. The process as claimed in claim 11 wherein the deprotectant is 20% piperidine in DMF.

* * * * *